United States Patent [19]

Ricks et al.

[11] Patent Number: 5,338,856
[45] Date of Patent: Aug. 16, 1994

[54] 3,4-N,TRISUBSTITUTED-4,5-DIHYDRO-1H-PYRAZOLE-1-CARBOXAMIDES AND THEIR USE AS INSECTICIDES

[75] Inventors: Michael J. Ricks, Concord; Yulan C. Tong, Walnut Creek, both of Calif.

[73] Assignee: DowElanco, Indianapolis, Ind.

[21] Appl. No.: 931,098

[22] Filed: Aug. 17, 1992

[51] Int. Cl.$^5$ .................. C07D 277/24; C07D 263/32
[52] U.S. Cl. .................. 548/204; 548/214; 548/236; 548/247
[58] Field of Search ................ 548/204, 214, 236, 247

[56] References Cited

U.S. PATENT DOCUMENTS

| | | | |
|---|---|---|---|
| 3,991,073 | 11/1976 | Mulder et al. | 260/310 |
| 4,070,365 | 1/1978 | van Daalen et al. | 548/379 |
| 4,174,393 | 11/1979 | van Daalen et al. | 424/250 |
| 4,839,376 | 6/1989 | Yamashita et al. | 514/406 |
| 4,863,947 | 9/1989 | Jacobson | 514/403 |
| 4,888,340 | 12/1989 | Neh et al. | 514/403 |
| 4,960,784 | 10/1990 | Lahm | 514/403 |
| 5,070,098 | 12/1991 | Fuchs et al. | 514/359 |

FOREIGN PATENT DOCUMENTS 466408 1/1992 European Pat. Off. .

OTHER PUBLICATIONS

Kantlehner, Chem. Zeitung 113 217 (1989), Abstract.

*Primary Examiner*—Robert Gerstl
*Attorney, Agent, or Firm*—D. Wendell Osborne

[57] ABSTRACT

3,4,N-Trisubstituted-4,5-dihydro-1H-pyrazole-1-carboxamide compounds wherein the substituent in the 4-position is a 5-membered heterocyclic ring moiety containing one ring oxygen or sulfur atom and one or two ring nitrogen atoms and the substituents in the 3-position and the N-position are optionally substituted phenyl moieties, such as 4,5-dihydro-3-(4-fluorophenyl)-N-(4-trifluoromethylphenyl)-4-(2-trifluoromethyl-5-thiazolyl)-1H-pyrazole-1-carboxamide were prepared from appropriate 3,4-disubstituted-4,5-dihydro-1H-pyrazole compounds, such as 4,5-dihydro-3-(4-fluorophenyl)-4-(2-trifluoromethyl-5-thiazolyl)-1H-pyrazole and phenyl isocyanates and isothiocyanates, such as 4-(trifluoromethyl)phenyl isocyanate. The compounds are insecticidal.

5 Claims, No Drawings

3,4-N,TRISUBSTITUTED-4,5-DIHYDRO-1H-PYRAZOLE-1-CARBOXAMIDES AND THEIR USE AS INSECTICIDES

BACKGROUND OF THE INVENTION

The present invention relates to 3,4,N-trisubstituted-4,5-dihydro-1H-pyrazole-1-carboxamide compounds wherein the substituent in the 4-position is a 5-membered heterocyclic ring moiety and the substituents in the 3-position and the N-position are optionally substituted phenyl moieties and to the insecticidal utility of these compounds.

The control of insects is critical to modern agriculture and to the maintenance of public health. Although many compounds that control insects are known, the discovery of new insecticides that are more effective, less toxic to man and the environment, less expensive to manufacture, or have other outstanding attributes are constantly sought and when found highly valued.

Certain 3,4,N-trisubstituted-4,5-dihydro-1H-pyrazole-1-carboxamide compounds wherein the 4-position substituent is an optionally substituted pyrazolyl or 1,2,4-triazolyl moiety that is attached to the dihydropyrazoline moiety at a ring nitrogen atom, are disclosed in U.S. Pat. No. 5,070,098. Certain N-aryl-3-phenyl-4-aryl-4-(alkyl or alkoxycarbonyl)-4,5-dihydro-1H-pyrazole-1-carboxamide compounds are disclosed generically in U.S. Pat. No. 4,863,947 and an example wherein the 4-aryl moiety is 2-benzoxazolyl and the other 4-substituent is methyl is described. Certain 3,5,N-trisubstituted pyrazoline-1-carboxamide compounds wherein the substituents in the 5-position are selected from certain pyridinyl, thienyl, furyl, and pyrryl moieties as well as certain phenyl moieties are generically disclosed in U.S. Pat. No. 3,991,073.

SUMMARY OF THE INVENTION

It has now been found that novel 3,4,N-trisubstituted-4,5-dihydro-1H-pyrazole-1-carboxamide compounds wherein the substituent in the 4-position is a 5-membered heterocyclic ring moiety containing a ring oxygen or sulfur atom and one or two ring nitrogen atoms, such as an optionally substituted oxazolyl, isoxazolyl, thiazolyl, isothiazolyl, oxadiazolyl, or thiadiazolyl moiety, and the substituents in the 3-position and the N-position are optionally substituted phenyl moieties possess excellent insecticidal utility.

In particular, 3,4,N-triaryl-4,5-dihydro-1H-pyrazole-1-carboxamide compounds of Formula I:

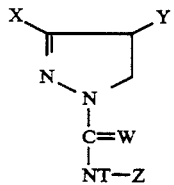

Formula I wherein

Y represents a 5-membered aromatic heterocyclic ring moiety containing one ring oxygen or sulfur atom and one or two ring nitrogen atoms, which moiety is attached through a carbon atom and is optionally substituted with one substituent selected from F, Cl, Br, CN, COQ, R, OR', SR', SOR', SO$_2$R', NO$_2$, and OAr and, in those moieties containing only one ring nitrogen atom, optionally additionally substituted with a F substituent;

X represents phenyl optionally substituted in the 4-position with F, Cl, Br, CN, COQ, R, OR', SR', SOR', SO$_2$R', NO$_2$, or OAr and/or in the 3-position with F, Cl, Br, CN, R, or OR';

Z represents phenyl optionally substituted in the 4-position with F, Cl, Br, CN, COQ, R, OR', SR', SOR', SO$_2$R', OSO$_2$R', NO$_2$, or OAr, in the 2-position with F, and in the 3- or 5-position with F, Cl, Br, CN, R, or OR';

T represents H, R", C(W)R, C(W)WR", SAr, SNR"R''', SM, or CH$_2$OR";

each W independently represents O or S;

R represents C$_1$-C$_3$ alkyl, C$_2$-C$_3$ alkenyl, or C$_2$-C$_3$ alkynyl optionally singly to completely substituted with fluorine or chlorine;

R' represents C$_1$-C$_3$ alkyl optionally singly to completely substituted with fluorine or chlorine;

R" represents C$_1$-C$_{18}$ alkyl, C$_3$-C$_{18}$ alkenyl, or C$_3$-C$_{18}$ alkynyl;

R''' represents R", C(W)WR", or C(W)R";

M represents a 5- to 7-membered saturated aliphatic nitrogen heterocycle which is attached to the S atom of SM at an N atom and which, optionally, contains an additional N heteroatom or a S or O heteroatom;

Ar represents phenyl optionally substituted with 1 or 2 compatible substituents selected from F, Cl, Br, CN, COQ, R, OR', SR', SOR', SO$_2$R', and NO$_2$;

Q represents OR$^2$, SR$^2$, NH$_2$, NHR$^2$, or NR$^2$$_2$; and

R$^2$ represents C$_1$-C$_4$ alkyl, C$_3$-C$_4$ alkenyl, or C$_3$-C$_4$ alkynyl were prepared and found to possess surprisingly good insecticidal properties. The compounds are typically employed as mixtures containing an insecticidal amount in combination with an agriculturally acceptable adjuvant or carrier.

3,4,N-Triaryl-4,5-dihydro-1H-pyrazole-1-carboxamide compounds of Formula I wherein the 5-membered ring heterocyclyl moiety is an oxazole, thiazole, 1,3,4-oxadiazole, or 1,3,4-thiadiazole ring that is attached to the dihydropyrazole ring at one position adjacent to the oxygen or sulfur atom and possesses one of the designated substituents in the other position adjacent to the oxygen or sulfur atom are often of particular interest.

The invention includes certain intermediates involved in preparing the novel insecticidal compounds of Formula I, including precursor optionally substituted 1-phenyl-2-(5-membered aromatic ring moiety containing a ring oxygen or sulfur atom and one or two ring nitrogen atoms heterocyclyl)ethanone compounds.

DETAILED DESCRIPTION OF THE INVENTION

The compounds of the present invention are 3,4,N-triaryl-4,5-dihydro-1H-pyrazole-1-carboxamide compounds of Formula I. 4,5-Dihydro-1H-pyrazole compounds are sometimes informally referred to as 2-pyrazoline or Δ2-pyrazoline compounds.

Compounds of Formula I exist in two enantiomeric isomer forms because the 4-position ring carbon atom is asymmetrically substituted. The present invention relates to each of the enantiomeric isomers and to all mixtures of these isomers. It is anticipated that the enantiomeric isomers will both have utility as insecticides but that one of the enantiomeric isomers will be generally more efficacious than the other.

The compounds of Formula I that are the subject of the present invention are characterized particularly in that Y represents a 5-membered aromatic heterocyclic ring moiety containing one ring oxygen or sulfur atom and one or two ring nitrogen atoms, which moiety is attached through a carbon atom and is optionally substituted with one substituent selected from F, Cl, Br, CN, COQ, R, OR', SR', SOR', SO$_2$R', NO$_2$, and OAr and, in those moieties containing only one ring nitrogen atom, optionally additionally substituted with a F substituent. R as used herein represents $C_1$–$C_3$ alkyl, $C_2$–$C_3$ alkenyl, or $C_2$–$C_3$ alkynyl optionally singly to completely substituted with fluorine or chlorine and R' represents $C_1$–$C_3$ alkyl optionally singly to completely substituted with fluorine or chlorine.

Representative 4-position 5-membered ring heterocyclyl moieties (Y) include optionally substituted thiazolyl, oxazolyl, isothiazolyl, isoxazolyl, 1,3,4-thiadiazolyl, 1,3,4-oxadiazolyl, 1,2,4-thiadiazolyl, and 1,2,4-oxadiazolyl moieties. Optionally substituted thiazolyl, oxazolyl, 1,3,4-thiadiazolyl, and 1,3,4-oxadiazolyl moieties are often preferred. Thiazolyl, oxazolyl, 1,3,4-thiadiazolyl, and 1,3,4-oxadiazolyl moieties attached to the dihydropyrazole ring at one position adjacent to the oxygen or sulfur atom and possessing a substituent in the other position adjacent to the oxygen or sulfur atom are often more preferred Y moieties. Such compounds wherein the substituent is selected from F, Cl, Br, CN, OCF$_3$, OCF$_2$H, and CF$_3$ are often most preferred.

X in Formula I represents phenyl optionally substituted in the 4-position with F, Cl, Br, CN, COQ, R, OR', SR', SOR', SO$_2$R', NO$_2$, or OAr and/or in the 3-position with F, Cl, Br, CN, R, or OR'. Similarly, Z represents phenyl optionally substituted in the 4-position with F, Cl, Br, CN, COQ, R, OR', SR', SOR', SO$_2$R', OSO$_2$R', NO$_2$, or OAr, in the 2-position with F, and in the 3- or 5-position with F, Cl, Br, CN, R, or OR'. Compounds wherein X and Z independently represent phenyl substituted in the 4-position with F, Cl, Br, CF$_3$, OCF$_3$, OCF$_2$H, OCF$_2$CF$_2$H, SO$_2$CF$_3$, or SCF$_3$ are often preferred.

T in Formula I represents H, R'', C(W)R, C(W)WR'', SAr, SNR''R''', SM, or CH$_2$OR'', wherein R'' represents $C_1$–$C_{18}$ alkyl, $C_3$–$C_{18}$ alkenyl, or $C_3$–$C_{18}$ alkynyl, and R''' represents R'', C(W)WR'', or C(W)R''. As used herein the letter W represents O or S, M represents a 5- to 7-membered saturated aliphatic nitrogen heterocycle which is attached to the S atom of SM at an N atom and which, optionally, contains an additional N heteroatom or a S or O heteroatom, Ar represents phenyl optionally substituted with 1 or 2 compatible substituents selected from F, Cl, Br, CN, COQ, R, OR', SR', SOR', SO$_2$R', and NO$_2$; and Q represents OR$^2$, SR$^2$, NH$_2$, NHR$^2$, or NR$^2{}_2$ where R$^2$ represents $C_1$–$C_4$ alkyl, $C_3$–$C_4$ alkenyl, or $C_3$–$C_4$ alkynyl. Compounds of Formula I wherein T represents hydrogen and W represents O are generally preferred. Compounds of Formula I wherein W represents S or wherein T represents other than hydrogen are believed to be converted to compounds wherein W represents O and T represents hydrogen in the environment or within insects and are considered to be pro-insecticides. Certain of these compounds, however, are believed to possess at least some insecticidal properties in the absence of any chemically or biologically induced reaction.

Some specifically preferred compounds of Formula I include 4,5-dihydro-3-(4-fluorophenyl)-N-(4-trifluoromethylphenyl)-4-(2-trifluoromethyl-5-thiazolyl)-1H-pyrazole-1-carboxamide, 4-(5-chloro-2-thiazolyl)-4,5-dihydro-3-(4-fluorophenyl)-N-(4-trifluoromethoxyphenyl)-1H-pyrazole-1-carboxamide, 4-(5-chloro-2-thiazolyl)-4,5-dihydro-3-(4-fluorophenyl)-N-(4-trifluoromethylphenyl)-1H-pyrazole-1-carboxamide, 3-(4-chlorophenyl)-4,5-dihydro-N-(4-trifluoromethoxyphenyl)-4-(2-trifluoromethyl-5-thiazolyl)-1H-pyrazole-1-carboxamide, 4,5-dihydro-3-(4-fluorophenyl)-N-(4-trifluoromethylphenyl)-4-(2-trifluoromethyl-5-oxazolyl)-1H-pyrazole-1-carboxamide, 3-(4-chlorophenyl)-4,5-dihydro-N-(4-trifluoromethoxyphenyl)-4-(3-trifluoromethyl-5-isothiazolyl)-1H-pyrazole-1-carboxamide, and 4,5-dihydro-3-(4-fluorophenyl)-N-(4-trifluoromethoxyphenyl)-4-(3-trifluoromethyl-5-isothiazolyl)-1H-pyrazole-1-carboxamide.

The 3,4-disubstituted-4,5-dihydro-1H-pyrazole-1-carboxamide compounds of Formula I wherein T represents H can be prepared by the reaction of an appropriate 3,4-disubstituted-4,5-dihydro-1H-pyrazole compound of Formula II with an appropriate isocyanate or isothiocyanate compound of Formula III as illustrated below.

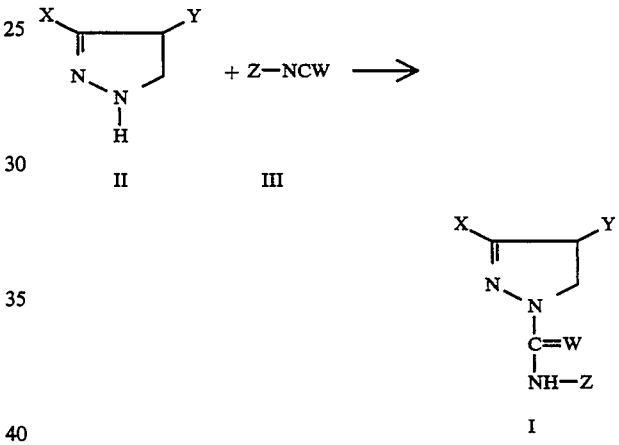

In Formulas II and III, W, X, Y, and Z are defined as hereinbefore for the compounds of Formula I. The reaction is generally effected by combining the 3,4-disubstituted-4,5-dihydro-1H-pyrazole and the isocyanate or isothiocyanate in the presence of an inert organic solvent, such as methylene chloride, 1,2-dichloroethane, chlorobenzene, toluene, acetonitrile, and the like, at a temperature of about 0° C. to about 60° C. and, typically, with agitation. The reaction takes place fairly rapidly, usually in about 0.1 to 20 hours. The 3,4,N-trisubstituted-4,5-dihydro-1H-pyrazole-1-carboxamide and thiocarboxamide products are solids and can be recovered by conventional means, such as by filtration, centrifugation, or removal of the volatiles by evaporation. The initially recovered products can be further purified by conventional means, such as by recrystallization.

The compounds of Formula I wherein T represents R''', C(W)R, C(W)WR'', SAr, SNR''R''', SM, or CH$_2$OR'' can be prepared from the corresponding compound of Formula I wherein T represents H by treatment with a base, such as sodium hydride or potassium carbonate, and then an appropriate alkylating, acylating, or sulfenylating agent, such as acetyl chloride, trifluoroacetic anhydride, ethyl chloroformate, (N-methyl-N-ethoxycarbonyl)aminosulfenyl chloride, 4-nitrophenylsulfenyl chloride, or butyloxymethyl chloride, in a solvent, such as N,N-dimethylformamide, tetrahydrofuran, or acetonitrile. The mixture is allowed to react at about ambient or an elevated temperature and the product is recovered by conventional means.

The appropriate 3,4-disubstituted 4,5-dihydro-1H-pyrazole compounds of Formula I can be prepared by treatment of an appropriately substituted propenone compound of Formula IV with hydrazine.

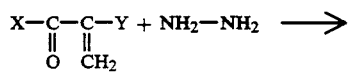

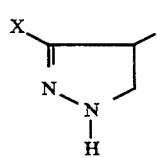

II

The reaction is typically effected by adding hydrazine, usually as the hydrate, to a solution of the propenone in a solvent, such as N,N-dimethylformamide or trifluoroacetic acid, at temperatures of about −20° C. to about 60° C. with agitation. After a reaction period of about 1 to about 8 hours the mixture is poured onto a mixture of ice and water with vigorous stirring. The desired product is typically recovered by extraction into an immiscible organic solvent, such as ether, and, if desired, further isolated by evaporation of the solvent. In those cases where the desired product precipitates as a solid, it can be recovered by filtration.

Compounds of Formula II are frequently unstable and degrade on attempted recrystallization or distillation. Accordingly, the crude products obtained are generally not recovered in pure form before being employed as intermediates. It is often preferred to further treat a solution in a water-immiscible organic solvent by washing with water or an aqueous solution and drying, and to employ the compound of Formula II in the form of the purified solution obtained.

The propenone compounds of Formula IV can be prepared by the reaction of bisdimethylaminomethane and acetic anhydride with the appropriately substituted ethanone compound of Formula V.

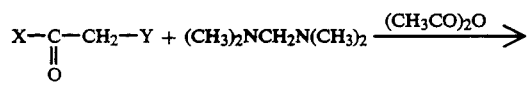

V

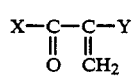

IV

The reaction is generally carried out by adding excess acetic anhydride to a mixture of the ethanone compound of Formula V in excess bisdimethylaminomethane at about 0° C. with agitation. The desired propenone compound of Formula IV can be recovered by conventional means, such as by adding water and ether, separating the phases, and evaporating the volatile materials from the ethereal phase.

Alternately and preferably, the 3,4-disubstituted-4,5-dihydro-1H-pyrazole compounds of Formula II can be prepared from 1,2-disubstituted ethanone compounds of Formula V in a one-pot process involving an intermediate Mannich adduct. The process can be carried out by combining an appropriate ethanone compound in an optionally chlorinated hydrocarbon solvent with an approximately equimolar amount of an N,N,N',N'-tetra($C_1$-$C_3$)alkyldiaminomethane, N,N',N''-tri($C_1$-$C_3$)alkylhexahydro-1,3,5-triazine, dipiperdinomethane, or dipyrrolidinylmethane compound and an approximately equimolar amount of an acid or anhydride of the formula

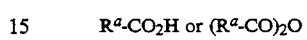

wherein $R^a$ represents ($C_1$-$C_4$)alkyl or phenyl, each optionally monosubstituted to completely substituted with F or Cl, or H at about −10° C. to about 30° C. to obtain an intermediate Mannich adduct of the formula:

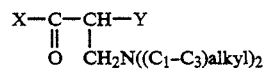

wherein X and Y are as defined for compounds of Formula I, and, without isolation, adding hydrazine at about 0° C. to about 50° C., optionally in the presence of an added catalytic amount of a strong acid, to obtain a compound of Formula II wherein each of the substituents are defined as hereinbefore.

In the first step of the above process the optionally chlorinated hydrocarbon solvent is, for example, dichloromethane, chloroform, trichloroethylene, or 1,1,1-trichloroethane. Chlorinated one or two carbon solvents, especially dichloromethane or chloroform, are typically preferred. The alkyl groups of the N,N,N',N'-tetra($C_1$-$C_3$)alkyldiaminomethane and N,N',N''-tri($C_1$-$C_3$)-alkylhexahydro-1,3,5-triazine compounds may be methyl, ethyl, propyl, or methylethyl alkyl groups. Methyl is preferred and N,N,N',N'-tetramethyldiaminomethane is especially preferred. Suitable acids and anhydrides include formic, acetic, propionic, trifluoroacetic, dichloroacetic, and the like. Acetic anhydride or trifluoroacetic acid are sometimes preferred. The term "approximately equimolar" includes at least molar ratios between about 1.25:1 and about 0.75:1. Mole ratios of about 1.1:1 to about 0.9:1 are more typical. The best results are often obtained at temperatures of about 0° C. to about 30° C. The reaction mixture is typically agitated.

In the second step of the above process the catalytic strong acid can be any acid having a pKa of about 2 or less that is readily soluble in the medium. Suitable strong acids include trifluoroacetic acid, dichloroacetic acid, methanesulfonic acid, and the like. Trifluoroacetic acid is often preferred. A catalytic amount is typically between about 1 and about 50 mole percent of the starting material ethanone. The hydrazine can be in any form, but is preferably anhydrous hydrazine. The best results are often obtained at temperatures of about 10° C. to about 40° C. The reaction mixture is typically agitated.

The compounds of Formula II prepared in the above manner can, with or without isolation, be treated with an optionally substituted phenyl isocyanate or isothiocyanate compound to obtain the insecticidal 3,4,N-triaryl-4,5-dihydro-1H-pyrazole-1-carboxamide compounds of Formula I as described hereinabove. When the compounds of Formula II are not isolated, the crude product is typically diluted with an inert, water-immiscible solvent, such as ether or dichloromethane, and the resulting solution is extracted with water or an aqueous solution and dried.

Certain of the ethanone compounds of Formula V can be obtained by the reaction of an acetyl compound of Formula VI with a substituted thiazole, oxazole, isothiazole, isoxazole, thiadiazole, or oxadiazole compound of Formula VII wherein E represents a fluoro, chloro, benzenesulfonyl, alkanesulfonyl or other moiety that is susceptible to displacement.

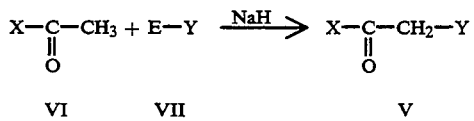

This method is especially valuable for the preparation of compounds of Formula V wherein Y is an optionally substituted thiazole or isothiazole moiety. The reaction can be carried out by adding a solution of the acetyl compound VI to a slurry of sodium hydride in an inert solvent, such as tetrahydrofuran or toluene, with agitation. The resultant mixture is maintained at about 0° C. to 120° C., the compound of Formula VII is added, and the mixture is allowed to react. The mixture is then cooled, quenched with an acid, and the desired product is recovered by conventional means.

Other of the ethanone compounds of Formula V can be obtained by the reaction of a compound of Formula VIII wherein X is defined as above and G represents an alkoxycarbonyl, N,N-dialkylcarbonyl, or cyano group with a methyl substituted heterocyclic compound of Formula IX wherein Y is as defined above.

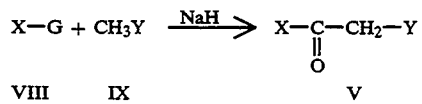

The reaction can be carried out by allowing the compound of Formula IX to react with a strong base, such as sodium hydride, butyl lithium, or lithium diisopropylamide, in an inert solvent, such as tetrahydrofuran, adding the compound of Formula VIII, and allowing the mixture to react. The resultant reaction mixture is quenched with an acid, such as hydrochloric acid, or an acidic salt, such as ammonium chloride, and the desired product is recovered by conventional means.

Alternately, compounds of Formula V can be prepared from a compound of Formula IX and a benzaldehyde-trimethylsilyl cyanide adduct compound of Formula X. The methyl compound of Formula IX is first brominated or chlorinated by a standard procedure and the bromomethyl or chloromethyl compound of Formula XI obtained is condensed with the compound of Formula X in the presence of a very strong base, such as lithium diisopropylamide. The resulting cyanohydrin is hydrolyzed by treatment with an aqueous acid and then an aqueous base to obtain the desired compound of Formula V.

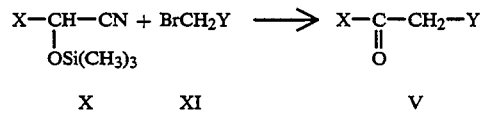

Most of the compounds of Formulas III, VI, VII, VIII, IX, and X are well known in the art or can be prepared by procedures well known in the art. The preparations of previously unknown compounds 5-methyl-2-trifluoromethyloxazole, 5-bromomethyl-2-trifluoromethyloxazole, 5-methyl-2-trifluoromethylthiazole, 5-bromomethyl-2-trifluoromethylthiazole, 5-methylthio-3-trifluoromethylisothiazole, and 5-methylsulfonyl-3-trifluoromethylisothiazole are given in the Experimental section.

The compounds of Formula I can be used directly to kill insects, but it is generally preferable to first prepare an insecticidal composition containing one or more of the compounds in combination with an agriculturally acceptable adjuvant or carrier. Suitable adjuvants or carriers should not be phytotoxic to valuable crops, particularly at the concentrations employed in applying the compositions for insect control in the presence of crops, and should not react chemically with the dihydropyrazole compound active ingredients or other composition ingredients. Such mixtures can be designed for direct application or can be concentrates or formulations which are normally diluted with additional carriers and adjuvants before application. They can be solids, such as, for example, dusts, granules, water dispersible granules, or wettable powders, or liquids, such as, for example, emulsifiable concentrates, solutions, emulsions, or suspensions.

Suitable agricultural adjuvants and carriers that are useful in preparing the insecticidal mixtures of the invention are well known to those skilled in the art.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, isopropyl alcohol, amyl alcohol, ethylene glycol, propylene glycol, glycerine, and the like. Water is generally the carrier of choice for the dilution of concentrates.

Suitable solid carriers include talc, pyrophyllite clay, silica, attapulgus clay, kieselguhr, chalk, diatomaceous earth, lime, calcium carbonate, bentonite clay, Fuller's earth, cotton seed hulls, wheat flour, soybean flour, pumice, wood flour, walnut shell flour, lignin, and the like.

It is frequently desirable to incorporate one or more surface-active agents into the compositions of the present invention. Such surface-active agents are advantageously employed in both solid and liquid compositions, especially those designed to be diluted with carrier before application. The surface-active agents can be anionic, cationic, or nonionic in character and can be employed as emulsifying agents, wetting agents, suspending agents, or for other purposes. Typical surface-active agents include salts of alkyl sulfates, such as diethanolammonium lauryl sulfate; alkylarylsulfonate salts, such as calcium dodecyl-benzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalenesulfonate salts, such as sodium dibutyl-naphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethyl-ammonium chloride; polyethylene glycol esters of fatty acids, such as polyethylene glycol stearate; block copolymers of ethylene oxide and propylene oxide; and salts of mono and dialkyl phosphate esters.

Other adjuvants commonly utilized in agricultural compositions include antifoam agents, compatibilizing agents, sequestering agents, neutralizing agents and buffers, corrosion inhibitors, dyes, odorants, penetration aids, spreading agents, sticking agents, dispersing agents, thickening agents, freeze point depressants, antimicrobial agents, and the like. The compositions can also contain other compatible components, for example, other insecticides or fungicides, herbicides, and the like and can be formulated with solid, particulate fertilizer carriers such as ammonium nitrate, urea and the like or with liquid fertilizers.

The concentration of the active ingredients of Formula I in the insecticidal compositions of this invention is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably about 10 to about 90 weight percent. Such compositions are typically diluted with an inert carrier, such as water, before application. The diluted compositions usually applied to insects or their locus generally contain about 0.001 to about 5 weight percent active ingredient and preferably contain about 0.01 to about 1.0 percent. Granular formulations containing about 1 to about 25 percent active ingredient are often employed and applied without further dilution.

The present compositions can be applied by the use of conventional ground or aerial dusters and sprayers, and by other conventional means known to those skilled in the art.

The insecticidal 3,4,N-triaryl-4,5-dihydro-1H-pyrazole-1-carboxamide compounds Formula I are useful for the kill and control of a wide variety of insects and can be employed to protect crops and livestock as well as buildings and the public health. Insects that live on foliage, in the soil, and in other environments can be controlled. Insects of the orders Lepidoptera, Coleoptera, Orthoptera, Isoptera, Hymenoptera, and Diptera are generally controlled. Lepidopterous insects of the genera Heliothis and Spodoptera, orthopterous insects of the genus Blattella, isopterous insects of the families Kalotermitidae, Hodotermitidae, and Rhinotermitidae, and hymenopterous insects of the family Formicidae are usually especially well controlled. Such insects include tobacco budworms, beet armyworms, German cockroaches, subterranean termites, and Formosan termites. The control of insects infesting crops, such as corn, cotton, rice, wheat, soybeans, and vegetables, is a preferred use of these compounds. The control of insects infesting homes and commercial buildings is another preferred use of the compounds. control of insects is generally achieved when at least about 0.01 kg/Ha is applied to foliage or other surfaces or when at least about 0.1 kg/Ha is applied to soil.

The method of killing or controlling insects by the application of compounds of Formula I is generally predicated on causing a compound of Formula I wherein T represents H to be present within the insects. This can be accomplished by applying to the insects or their locus compounds of Formula I wherein T represents H directly or by applying a compound of Formula I wherein T represents R'', C(W)R, C(W)WR'', SAr, SNR''R''', SM, or CH$_2$OR''. It is also possible to cause an insecticidal amount of such a compound to be present within insects by applying other derivative compounds, wherein T represents other than H, which compounds are converted within the insects or in the environment to a compound of Formula I wherein T represents H. The required conversions take place by natural chemical processes, such as hydrolysis, oxidation, reduction, and the like, that are either enzymatic or non-enzymatic in nature.

EXPERIMENTAL

General. Reagents and solvents were used as purchased from commercial suppliers. All reactions involving organometallic reagents were conducted in a dry nitrogen atmosphere using oven-dried glassware. Melting points were taken on a Gallenkamp or Thomas Hoover apparatus and were uncorrected. Proton nuclear magnetic resonance spectroscopy (1H NMR) was performed using a Varian XL200 or Brucker AM400 spectrometer in CDCl$_3$ as solvent, unless otherwise noted. 1H NMR data are presented as: chemical shift in parts per million (ppm) downfield from tetramethylsilane (multiplicity, number of hydrogens, coupling constant(s) in Hertz (Hz)). Carbon nuclear magnetic resonance (13C NMR) was performed using a Brucker AM400 spectrometer operating at 101 megaHertz in CDCl$_3$ solvent, unless otherwise noted.

EXAMPLE 1

Preparation of 5-Methylsulfonyl-3-(trifluoromethyl)isothiazole

A. Preparation of Ethyl 5-Methylthio-3-(trifluoromethyl)isothiazole-4-carboxylate The general procedure of Krebs, *Aust. J. Chem.*, 42, 1291 (1989), was employed. Ethyl 3-amino-4,4,4-trifluorocrotonate (9.16 g (gram), 50 mmol (millimole)) was dissolved in 30 mL (milliliter) of N,N-dimethylformamide and 1.2 g of 60 percent in mineral oil sodium hydride (50 mmol) was added in small portions with stirring and cooling to keep the temperature around 25° C. The mixture was stirred for about 1 hr (hour) until the evolution of gas had essentially ceased and was then cooled to −7° C. Carbon disulfide (4.19 g, 55 mmol) in 4 mL of N,N-dimethylformamide was then added slowly with stirring maintaining the temperature below 10° C. by cooling. The mixture was then allowed to warm to 15° C. and 8.29 g (60 mmol) of iodomethane in 4 mL of N,N-dimethylformamide was added with stirring. After 15 min (minutes) the reaction mixture was poured onto 75 g of ice. The red oil that formed was extracted into 2×75 mL of ether. The ethereal solution, dried over sodium sulfate, filtered, and concentrated by evaporation under reduced pressure and the residue was dissolved in 50 mL of ethanol and 7.91 g (100 mmol) of pyridine. A solution prepared by dissolving 12.7 g (50 mmol) of iodine and 20.75 g (125 mmol) of potassium iodide in 100 mL of water was added to this slowly with stirring. The precipitate that formed was collected by filtration and dissolved in ether. The ethereal solution was washed with water and 2×60 mL of 0.5N aqueous sodium thiosulfate solution, dried over sodium sulfate, filtered, and concentrated by evaporation under reduced pressure. The residue was recrystallized from hexane to obtain 5.7 g (42 percent of theory) of the title compound as a solid melting at 64°–65° C.

Elemental Analysis for $C_8H_8F_3NO_2S_2$: Calc.: %C, 35.4; %H, 2.97; %N, 5.16; %S, 23.6; Found: %C, 35.6; %H, 2.99; %N, 5.18; %S, 23.7.

B. Preparation of 5-Methylthio-3-(trifluoromethyl)isothiazole-4-carboxylic Acid

A 5.2 g (19.2 mmol) sample of ethyl 5-methylthio-3-(trifluoromethyl)isothiazole-4-carboxylate was combined with 1.39 g (21 mmol) of 85 percent potassium hydroxide and 25 mL of 95 percent ethanol and the mixture was heated on a steam bath for 45 min and then concentrated under reduced pressure to remove the volatiles. The residue was dissolved in water and acidified with concentrated hydrochloric acid. The white precipitate that formed was collected by filtration and dissolved in a mixture of acetone and ether. The resulting solution was dried over sodium sulfate, filtered, and concentrated by evaporation under reduced pressure to obtain 3.75 g (80 percent of theory) of the title compound as a white solid melting at 260°–262° C.

Elemental Analysis for $C_6H_4F_3NO_2S_2$: Calc.: % C, 29.6; % H, 1.66; % N, 5.76; % S, 26.4 Found: % C, 29.7; % H, 1.62; % N, 5.73; % S, 26.3.

C. Preparation of 5-Methylthio-3-(trifluoromethyl)isothiazole

5-Methylthio-3-(trifluoromethyl)isothiazole-4-carboxylic acid (9.4 g, 39 mmol) was dissolved in 15 mL of quinoline and 0.6 g (4.2 mmol) of cuprous oxide was added. The mixture was heated at 170° C. for about 30 min and then allowed to cool. It was then diluted with ether and the resulting solution was washed with 100 mL of 2N hydrochloric acid, dried over sodium bicarbonate, filtered, and distilled to obtain 6.55 g (85 percent of theory) of the title compound as a colorless liquid boiling at 126°–127° C. at 84 mm Hg (11 kPa (kiloPascals)) pressure.

Elemental Analysis for $C_5H_4F_3NS_2$: Calc.: % C, 30.1; % H, 2.02; % N, 7.03; % S, 32.2 Found: % C, 30.3; % H, 1.88; % N, 7.03; % S, 32.3.

D. Preparation of 5-Methylsulfonyl-3-(trifluoromethyl)isothiazole

A 2.0 g (10 mmol) sample of 5-methylthio-3-(trifluoromethyl)isothiazole was added to 5 mL of trifluoroacetic acid and the solution was heated to 50° C. Thirty percent hydrogen peroxide (0.85 g, 25 mmol) was then added slowly with stirring at 50°–60° C. and heating was continued for about 45 min. The mixture was next poured onto 40 g of ice and the precipitate that formed was collected by filtration. It was then dissolved in dichloromethane and the solution dried over magnesium sulfate, filtered, and concentrated by evaporation under reduced pressure to obtain a solid residue. This was diluted with hexane and then recovered by filtration and dried to obtain 1.6 g (69 percent of theory) of the title compound as a white solid melting at 93°–94° C.

Elemental Analysis for $C_5H_4F_3NO_2S_2$: Calc.: % C, 26.0; % H, 1.74; % N, 6.06; % S, 27.7 Found: % C, 26.0; % H, 1.65; % N, 6.03; % S, 27.8.

EXAMPLE 2

Preparation of 1-(4-Chlorophenyl)-2-(3-(trifluoromethyl)-5-isothiazolyl)ethanone The oil of a 4.0 g (100 mmol) portion of 60 percent in mineral oil sodium hydride was removed by triple extraction with hexane and was replaced with 100 mL of tetrahydrofuran. 4-Chloroacetophenone (4.33 g, 28 mmol) was added and the mixture was heated at reflux with stirring for 1 hr and then allowed to cool. 5-Methylsulfonyl-3-(trifluoromethyl)isothiazole (4.57 g, 19.8 mmol) dissolved in a small amount of tetrahydrofuran was added and the mixture was heated at reflux with stirring for 3 hr and then allowed to cool. The mixture was next acidified with 60 mL of 10 percent aqueous acetic acid and the layers that formed were separated. The aqueous layer was extracted with 2×100 mL of ether and the organic fractions were combined, washed with aqueous sodium bicarbonate solution, dried over sodium sulfate, filtered, and concentrated by evaporation under reduced pressure to obtain a residue. This residue was washed with hexane and crystallized from a 1:1 mixture of dichloromethane and hexane to obtain 3.19 g (53 percent of theory) of the title compound as a solid melting at 109°–110° C.

Elemental Analysis for $C_{12}H_7ClF_3NOS$: Calc.: % C, 47.1; % H, 2.31; % N, 4.58; % S, 10.5 Found: % C, 47.4; % H, 2.42; % N, 4.56; % S, 10.3.

The following compounds were prepared similarly from 5-methylsulfonyl-3-(trifluoromethyl)isothiazole and an appropriately substituted acetophenone:

1-(4-fluorophenyl)-2-(3-(trifluoromethyl-5-isothiazolyl)ethanone, a solid melting at 103°–105° C. (59 percent yield);

Elemental Analysis for $C_{12}H_7F_4NOS$: Calc.: % C, 49.8; % H, 2.24; % N, 4.84; % S, 11.1 Found: % C, 49.8; % H, 2.33; % N, 4.81; % S, 11.4; and 1-(4-(trifluoromethyl)phenyl)-2-(3-(trifluoromethyl)-5-isothiazolyl)ethanone, a solid melting at 114°–115° C. (48 percent yield);

Elemental Analysis for $C_{13}H_7F_6NOS$: Calc.: % C, 46.0; % H, 2.08; % N, 4.13; % S, 9.45 Found: % C, 46.1; % H, 2.14; % N, 4.21; % S, 9.54.

EXAMPLE 3

Preparation of 2-(3-Methyl-5-isoxazolyl)-1-phenylethanone

The general procedure of Micetich, Can. J. Chem., 48, 2006 (1970) was employed. 3,5-Dimethylisoxazole (4.86 g, 50 mmol) and 100 mL of tetrahydrofuran were placed in a flask under nitrogen and cooled to −70° C. with an ether/Dry Ice bath. To this was added with cooling and stirring 20 mL (50 mmol) of 2.5M n-butyl lithium in hexane solution at a rate such that the temperature remained below −50° C. and the mixture was allowed to stir at −70° C. for 1 hr. Benzonitrile (5.67 g, 55 mmol) was then added and stirring at −70° C. was continued for an additional 2-hr period. The resulting mixture was allowed to warm to ambient temperature and was then concentrated by evaporation under reduced pressure. The residue was mixed with 100 mL of 1N hydrochloric acid and extracted with dichloromethane. The organic extract was dried over magnesium sulfate, filtered, and concentrated by evaporation under reduced pressure to obtain a solid residue which was recrystallized from ether to obtain 4.6 g (46 percent of theory) of the title compound as a yellow solid melting at 73°–74° C.

Elemental Analysis for $C_{12}H_{11}NO_2$: Calc.: % C, 71.6; % H, 5.51; % N, 6.96 Found: % C, 71.8; % H, 5.80; % N, 7.09.

The following were prepared similarly from 3,5-dimethylisoxazole and a substituted benzonitrile;

1-(4-chlorophenyl)-2-(3-methyl-5-isoxazolyl)ethanone, yellow crystals melting at 107°–109° C. (47 percent yield);

Elemental Analysis for $C_{12}H_{10}ClNO_2$: Calc.: % C, 61.2; % H, 4.28; % N, 5.94 Found: % C, 61.1; % H, 4.62; % N, 6.00: and 1-(4-fluorophenyl)-2-(3-methyl-5-isoxazolyl)ethanone, tan plates melting at 92°–93° C. (57 percent yield);

Elemental Analysis for $C_{12}H_{10}FNO_2$: Calc.: % C, 65.8; % H, 4.60; % N, 6.39 Found: % C, 65.7; % H, 4.69; % N, 6.69.

EXAMPLE 4

Preparation of 5-Methyl-2-trifluoromethyloxazole

Aminoacetone hydrochloride of about 80 percent purity (13.3 g, 121 mmol) was slurried in 100 mL of benzene and 22 mL (146 mmol) of trifluoroacetic anhydride was added with stirring. The mixture was heated at reflux for 2–3 hr, during which time it separated into two liquid phases, and was then allowed to cool. Sufficient diatomaceous earth was added to sequester the smaller lower phase as a white solid. This was collected by filtration and extracted with 2×50 mL of dichloromethane. The upper phase and the dichloromethane extracts were combined and distilled at 200 torr (27 kPa) through a short Vigreaux column until the head temperature reached 70° C. The residue was then kugelrohr distilled taking the fraction that distilled at 110° C. and 20 torr (2.7 kPa). This material, which solidified, was dissolved in 50 mL of phosphorus oxychloride and the mixture was heated at reflux for 2 hr during which time it turned very dark. The mixture was then distilled through a 15 cm Vigreaux column until the head temperature reached 110° C. The distillate, a water-white oil, was slowly added to 150 mL of water with vigorous stirring, keeping the temperature below 40° C. After 30 min the mixture was extracted with 3×50 mL of ether. The ethereal extract was dried over magnesium sulfate and distilled using a 30 cm glass helices packed column to remove the ether and other volatiles. Solid sodium bicarbonate was cautiously added to the residue until foaming ceased. The resulting slurry was filtered and the solids extracted with 3 mL of ether. The combined organics were distilled through a short Vigreaux column to obtain 1.75 g (9 percent of theory) of the title compound as a colorless oil containing about 10 percent ether as an impurity boiling at 100°–104° C. The proton NMR spectrum had absorptions at δ 2.36 (s, 3H) and 6.85 (s, 1H).

EXAMPLE 5

Preparation of 5-Bromomethyl-2-trifluoromethylthiazole

A. Preparation of Trifluoroacetamidoacetone

Aminoacetone hydrochloride (13.29 g, 121 mmol) was slurried in 200 mL of dichloromethane and stirred vigorously as 22 mL (146 mmol) of trifluoroacetic acid was added. The mixture was heated to reflux with stirring for about 1 hour at which time the evolution of gas had ceased. The resulting mixture was concentrated by evaporation at 60° C. and the residue was dissolved in 200 mL of ether. Solid sodium bicarbonate was cautiously added with stirring until foaming ceased. The resulting slurry was filtered through a 2×5 cm silica gel plug and the plug was eluted with an additional 100 mL of ether. The combined filtrates were concentrated by evaporation at temperatures up to 60° C. The residue was kugelrohr distilled at a pot temperature of 100°–110° C. and a pressure of 18 torr (2.4 kPa) to obtain 9.7 g (47 percent of theory) of the title compound as a waxy white solid. An analytical sample prepared by recrystallization from pentane was a white solid melting at 71°–73° C.

Elemental Analysis for $C_5H_6F_3NO_2$: Calc.: % C, 35.5; % H, 3.58; % N, 8.28 Found: % C, 35.6; % H, 3.69; % N, 8.22.

B. Preparation of 5-Methyl-2-trifluoromethylthiazole

Trifluoroacetamidoacetone (8.45 g, 50 mmol) and 20.2 g (50 mmol) of Lawesson's reagent were slurried in 100 mL of benzene and the mixture was heated at reflux with stirring for 4–5 hours to obtain a clear solution. This was allowed to cool and was washed with 50 mL of 10 percent aqueous sodium hydroxide solution, dried over magnesium sulfate, and filtered. The resulting solution was kugelrohr distilled at 160° C. and the distillate was distilled through a 40 cm column packed with glass helices (to remove the benzene) until the head temperature began to drop. It was then distilled through a 20 cm Vigreaux column to obtain 5.1 g (61 percent of theory) of the title compound as a pale oil boiling at 138°–141° C.

Elemental Analysis for $C_5H_4F_3NS$: Calc.: % C, 35.9; % H, 2.41; % N, 8.38; % S, 19.2 Found: % C, 36.1; % H, 2.55; % N, 8.53; % S, 18.9.

C. Preparation of 5-Bromomethyl-2-trifluoromethylthiazole

5-Methyl-2-trifluoromethylthiazole (2.26 g, 13.5 mmol), N-bromosuccinimide (2.64 g, 14.6 mmol), and 50 mL of benzene were placed in a jacketed flask and the resulting mixture was stirred and irradiated with a 250 Watt sun lamp placed 10 cm from the flask. The temperature rose from 25° to 40° C. After 3 hr an additional 0.26 g (1.5 mmol) of N-bromosuccinimide was added and the reaction continued another 30 min. Analysis of an aliquot by gas-liquid chromatography indicated that the mixture contained about 7 percent starting material, 73 percent title compound, and 17 percent dibrominated material. The mixture was extracted with 50 mL of 2 percent aqueous sodium hydroxide, dried over magnesium sulfate, filtered, and concentrated by evaporation under reduced pressure to obtain a yellow oil. This was purified by medium pressure liquid chromatography to obtain 1.86 g (56 percent of theory) of 5-bromomethyl-2-trifluoromethylthiazole as a pale yellow oil which was 97 percent pure by gas liquid chromatography. The proton NMR spectrum had absorptions at δ4.69 (s, 2H) and 7.87 (s, 1H).

5-Bromomethyl-2-trifluoromethyloxazole, which has a boiling point at 80°–90° C. under 25 torr (3.3 kPa) pressure, was prepared similarly and was recovered in 38 percent yield as an 85 percent pure compound containing 12 percent dibromo compounds and 2.5 percent benzene. The proton NMR spectrum had absorptions at δ4.47 (s, 2H) and 7.20 (s, 1H).

EXAMPLE 6

Preparation of 1-(4-Fluorophenyl)-2-(2-trifluoromethyl-5-thiazolyl)ethanone

A solution of 2.4M n-butyl lithium in hexane (6.4 mL, 15.4 mmol) was added to a solution of 2.15 mL (15.4 mmol) of diisopropylamine in 50 mL of dry tetrahydrofuran at −10° C. under nitrogen with stirring over a 2-min period. The resulting solution was cooled to −70° C. and a solution containing 3.18 g (14 mmol) of 2-(trimethylsilyloxy)-2-(4'-fluorophenyl)acetonitrile in 3 mL of dry tetrahydrofuran was added dropwise by means of a syringe pump over a 20-min period under nitrogen with stirring. The resulting bright yellow solution was stirred for an additional 30 min at −70° C. or below and then a solution of 2.92 g (11.9 mmol) of 5-bromomethyl-2-trifluoromethylthiazole in 5 mL of dry tetrahydrofuran was added over 30 min under nitrogen with stirring to obtain a dark, thick slurry. After a 45-min reaction period this mixture was allowed to warm and was poured into a rapidly stirred mixture consisting of 25 mL of 10 percent aqueous hydrochloric acid and 10 mL of methanol. Aqueous hydrofluoric acid (0.5 mL of 48 percent) was then added and the mixture was stirred until all of the trimethylsilane protecting group was removed. Sufficient 10 percent aqueous sodium hydroxide was added with stirring to adjust the pH to about 10 and after 15 min the phases were separated. The aqueous phase was extracted with 2×30 mL of ether and the combined organic phases were washed with 50 mL of 10 percent aqueous hydrochloric acid and 50 mL of saturated aqueous sodium chloride, dried over magnesium sulfate, and concentrated by evaporation under reduced pressure. The residue was kugelrohr distilled, first at 70° C. and 0.05 torr (6.7 Pa (Pascals)) to remove 4-fluorobenzaldehyde and then at 100°–110° C. and 0.05 torr (6.7 Pa) to distill 2.93 g (85 percent of theory) of the title compound, which was obtained as a waxy yellow solid of 95 percent purity (by gas liquid chromatography). An analytical sample obtained by crystallization from a mixture of hexane and acetone melted at 66.5°–68.5° C.

Elemental Analysis for $C_{12}H_7F_4NOS$: Calc.: % C, 49.8; % H, 2.44; % N, 4.84; % S, 11.1 Found: % C, 50.1; % H, 2.44; % N, 4.92; % S, 11.5.

1-(4-Fluorophenyl)-2-(2-trifluoromethyl-5-oxazolyl)ethanone was prepared similarly and was obtained as a yellow oil that distilled at 80° C. and 0.02 torr (2.7 Pa) pot temperature.

Elemental Analysis for $C_{12}H_7F_4NO_2$: Calc.: % C, 52.8; % H, 2.58; % N, 5.13 Found: % C, 52.7; % H, 2.77; % N, 5.10.

EXAMPLE 7

Preparation of 3-(4-Chlorophenyl)-4,5-di-hydro-N-(4-trifluoromethoxyphenyl)-4-(3-trifluoromethyl-5-isothiazolyl)-1H-pyrazole-1-carboxamide (Compound I-A)

A mixture of 5.0 mL of N,N,N', N'-tetramethyldiaminomethane and 3.06 g (10 mmol) of 1-(4-chlorophenyl)-2-(3-trifluoromethyl-5-isothiazolyl)ethanone were combined and chilled in an ice-salt bath to about 0° C. A 5.0 mL portion of acetic anhydride was added dropwise with stirring maintaining the temperature at less than 20° C. with cooling and the reaction was continued for an additional 45 min at which time the mixture was poured onto 40 g of ice. The oil that formed was recovered by extraction with 3×50 mL of ether and the ethereal extracts were combined, washed with aqueous sodium bicarbonate and aqueous sodium chloride solutions, dried over sodium sulfate, filtered, and concentrated by evaporation under reduced pressure to obtain 3 g of a glassy material. This was dissolved in 15 mL of trifluoroacetic acid with cooling to 0° C. and 1.41 g (28 mmol) of hydrazine monohydrate was added with stirring. After 2 min stirring, the mixture was diluted with ice water and filtered to recover the solid 3-(4-chlorophenyl)-4,5-dihydro-4-(3-trifluoromethyl-5-isothiazolyl)-1H-pyrazole that formed. This was dissolved in dichloromethane and the solution obtained was dried over sodium bicarbonate and sodium sulfate and was filtered. 4-Trifluoromethoxyphenyl isocyanate (1.91 g, 9.4 mmol) was added dropwise with stirring at ambient temperature and the resulting mixture was allowed to stand overnight. A 1.5 mL portion of acetic acid was added and the mixture was stirred for 30 min at which time it was washed with aqueous sodium bicarbonate solution, dried over sodium sulfate, filtered, and concentrated by evaporation under reduced pressure to obtain an oil. The residual oil was placed on a silica gel column and eluted with a 9:1 mixture of hexane and acetone to obtain 0.45 g (8.4 percent of theory) of the title compound as a solid melting at 101°–104° C.

Elemental Analysis for $C_{21}H_{13}ClF_6N_4O_2S$: Calc.: % C, 47.2; % H, 2.45; % N, 10.5; % S, 6.00 Found: % C, 47.2; % H, 2.67; % N, 10.2; % S, 6.10.

The following were prepared similarly from a 1-(substituted-phenyl)-2-(3-trifluoromethyl-5-isothiazolyl)ethanone and an isocyanate:

4,5-dihydro-3-(4-fluorophenyl)-4-(3-trifluoromethyl-5-isothiazolyl)-N-(4-trifluoromethoxyphenyl)-1H-pyrazole-1-carboxamide (Compound I-B), a white solid melting at 140°–143° C. (containing some hexane impurity) (8 percent yield);

Elemental Analysis for $C_{21}H_{13}F_7N_4O_2S$: Calc.: % C, 48.7; % H, 2.50; % N, 10.8; % S, 6.18 Found: % C, 49.4; % H, 2.60; % N, 10.3; % S, 6.01;

4,5-dihydro-3-(4-fluorophenyl)-4-(3-trifluoromethyl-5-isothiazolyl)-N-(4-trifluoromethylphenyl)-1H-pyrazole-1-carboxamide (Compound I-C), a white solid melting at 158°–159° C. (30 percent yield);

Elemental Analysis for $C_{21}H_{13}F_7N_4OS$: Calc.: % C, 50.2; % H, 2.61; % N, 11.2; % S, 6.38 Found: % C, 50.6; % H, 2.76; % N, 11.1; % S, 6.06; and 4,5-dihydro-N-(4-trifluoromethoxyphenyl)-4-(3-trifluoromethyl-5-isothiazolyl)-3-(4-trifluoromethylphenyl)-1H-pyrazole-1-carboxamide (Compound I-D), a white solid melting at 165°–166° C. (11 percent yield);

Elemental Analysis for $C_{22}H_{13}F_9N_4O_2S$: Calc.: % C, 46.5; % H, 2.30; % N, 9.86; % S, 5.64 Found: % C, 46.4; % H, 2.30; % N, 9.71; % S, 5.30.

EXAMPLE 8

Preparation of 4,5-Dihydro-4-(3-methyl-5-isoxazolyl)-3-phenyl-N-(4-trifluoromethoxyphenyl)-1H-pyrazole-1-carboxamide (Compound I-E)

A mixture of 20 mL of dichloromethane, 2.01 g (10 mmol) of 2-(3-methyl-5-isoxazolyl)-1-phenylethanone and 1.12 g (11 mmol) of N,N,N',N'-tetramethyldiaminomethane was prepared and cooled to −15° C. and 1.25 g (11 mmol) of trifluoroacetic acid in 5 mL of dichloromethane was added with cooling and stirring.

Stirring was continued for 5 min at about 0° C. and then the mixture was allowed to warm to ambient temperature and stir for another 1.75 hr. A proton NMR spectrum of the mixture was taken which indicated complete disappearance of the starting material. Anhydrous hydrazine (0.96 g, 30 mmol) was added and the mixture was allowed to react with stirring for 2 hr. A proton NMR spectrum of the mixture indicated complete conversion to 4,5-dihydro-4-(3-methyl-5-isoxazolyl)-3-phenyl-1H-pyrazole. The mixture was washed with saturated aqueous sodium bicarbonate solution, dried over sodium sulfate, and filtered. 4-(Trifluoromethoxy)phenyl isocyanate (2.19 g, 10.8 mmol) was then added with stirring. The mixture was allowed to react for 1 hr and then 1 mL of acetic acid was added and the mixture was allowed to react for 5 min. It was then washed with saturated aqueous sodium bicarbonate, dried over sodium sulfate, filtered, and concentrated by evaporation under reduced pressure. The resulting solid was extracted with boiling ether and air dried to obtain 3.1 g (72 percent of theory) of the title compound as a white solid melting at 195°–197° C.

Elemental Analysis for $C_{21}H_{17}F_3N_4O_3$: Calc.: % C, 58.7; % H, 3.97; % N, 13.0 Found: % C, 58.4; % H, 4.25; % N, 13.0.

The following were prepared similarly from 2-(3-methyl-5-isoxazolyl)-1-phenylethanone:

3-(4-chlorophenyl)-4,5-dihydro-4-(3-methyl-5-isoxazolyl)-N-(4-trifluoromethoxyphenyl)-1H-pyrazole-1-carboxamide (Compound I-F), a white solid melting at 155°–157° C. (34 percent yield);

Elemental Analysis for $C_{21}H_{16}ClF_3N_4O_3$: Calc.: % C, 54.3; % H, 3.47; % N, 12.1 Found: % C, 54.2; % H, 3.81; % N, 12.1;

4,5-dihydro-3-(4-fluorophenyl)-4-(3-methyl-5-isoxazolyl)-N-(4-trifluoromethoxyphenyl)-1H-pyrazole-1-carboxamide, (Compound I-G) a white solid melting at 172°–174° C. (58 percent yield);

Elemental Analysis for $C_{21}H_{16}ClF_3N_4O_3$: Calc.: % C, 56.3; % H, 3.60; % N, 12.5 Found: % C, 56.4; % H, 3.83; % N, 12.5; and 3-(4-chlorophenyl)-N-(4-chlorophenyl)-4,5-dihydro-4-(3-methyl-5-isoxazolyl)-1H-pyrazole-1-carboxamide (Compound I-H), a white solid melting at 163°–165° C. (65 percent yield);

Elemental Analysis for $C_{21}H_{16}ClF_3N_4O_3$: Calc.: % C, 57.8; % H, 3.88; % N, 13.5 Found: % C, 57.7; % H, 4.00; % N, 13.5.

EXAMPLE 9

Preparation of 4,5-Dihydro-3-(4-fluorophenyl)-N-(4-trifluoromethylphenyl)-4-(2-trifluoromethyl-5-thiazolyl)-1H-pyrazole-1-carboxamide (Compound I-P)

A solution of 112 uL (microliters) (1.1 mmol) of acetic anhydride and 289 mg (milligram) (1.0 mmol) of 1-(4-fluorophenyl)-2-(2-trifluoromethyl-5-thiazolyl)ethanone in 2 mL of chloroform was added to a solution of 136 uL (1.2 mmol) of N,N,N',N'-tetramethyldiaminomethane in 3 mL of chloroform with stirring over a 5-min period. The resulting solution was stirred for 10 min and then 46 uL (1.5 mmol) of anhydrous hydrazine and one drop of trifluoroacetic acid were added sequentially. The mixture was heated at reflux with stirring for 20–30 min and then was cooled and diluted to 20 mL with dichloromethane. The resulting solution was washed with 2×10 mL of water, dried over sodium sulfate, and filtered to obtain 4,5-dihydro-3-(4-fluorophenyl)-4-(2-trifluoromethyl-5-thiazolyl)-1H-pyrazole. 4-Trifluoromethylphenyl isocyanate (143 uL, 1.0 mmol) was then added and the mixture was heated at reflux for 15 min, cooled, and concentrated by evaporation under reduced pressure. The residue was purified by medium pressure liquid chromatography eluting with a 90:10 mixture of hexane and ether to obtain 297 mg (63 percent of theory) of the title compound as a white foamy solid. An analytical sample prepared by recrystallization from a mixture of hexane and acetone was a white solid melting at 174°–176° C.

Elemental Analysis for $C_{21}H_{13}F_7N_4OS$: Calc.: % C, 50.2; % H, 2.61; % N, 11.2; % S, 6.38 Found: % C, 50.1; % H, 2.51; % N, 11.1; % S, 6.39.

The following compounds were prepared similarly from 1-(4-fluorophenyl)-2-(2-trifluoromethyl-5-thiazolyl)ethanone, 1-(4-chlorophenyl)-2-(2-trifluoromethyl-5-thiazolyl)ethanone, or 1-(4-fluorophenyl)-2-(2-trifluoromethyl-5-oxazolyl)ethanone:

N-(4-chlorophenyl)-4,5-dihydro-3-(4-fluorophenyl)-4-(2-trifluoromethyl-5-thiazolyl)-1H-pyrazole-1-carboxamide (Compound I-I), a white solid melting at 187.5°–189.5° C. (57 percent yield);

Elemental Analysis for $C_{20}H_{13}ClF_4N_4OS$: Calc.: % C, 51.2; % H, 2.79; % N, 12.0; % S, 6.84 Found: % C, 51.2; % H, 2.82; % N, 11.7; % S, 6.63;

4,5-dihydro-3-(4-fluorophenyl)-N-(4-(1,1,2,2-tetrafluoroethoxy)phenyl)-4-(2-trifluoromethyl-5-thiazolyl)-1H-pyrazole-1-carboxamide (Compound I-J), a white solid melting at 171°–172° C. (55 percent yield);

Elemental Analysis for $C_{22}H_{14}F_8N_4O_2S$: Calc.: % C, 48.0; % H, 2.53; % N, 10.2; % S, 5.82 Found: % C, 47.9; % H, 2.60; % N, 10.1; % S, 6.01;

3-(4-chlorophenyl)-4,5-dihydro-N-(4-trifluoromethylphenyl)-4-(2-trifluoromethyl-5-thiazolyl)-1H-pyrazole-1-carboxamide (Compound I-L), a white solid melting at 213.5°–214.5° C. (50 percent yield);

Elemental Analysis for $C_{21}H_{13}ClF_6N_4OS$: Calc.: % C, 48.6; % H, 2.53; % N, 10.8; % S, 6.18 Found: % C, 48.3; % H, 2.47; % N, 10.7; % S, 5.85;

3-(4-chlorophenyl)-4,5-dihydro-N-(4-trifluoromethoxyphenyl)-4-(2-trifluoromethyl-5-thiazolyl)-1H-pyrazole-1-carboxamide (Compound I-K), a white solid melting at 174°–176° C. (51 percent yield);

Elemental Analysis for $C_{21}H_{13}ClF_6N_4O_2S$: Calc.: %C, 47.2; %H, 2.45; %N, 10.5; %S, 5.99 Found: %C, 47.3; %H, 2.36; %N, 10.4; %S, 5.66;

4,5-dihydro-3-(4-fluorophenyl)-4-(2-trifluoromethyl-5-oxazolyl)-N-(4-trifluoromethylphenyl)-1H-pyrazole-1-carboxamide (Compound I-M), a white solid melting at 178.5°–180.5° C. (39 percent yield);

Elemental Analysis for $C_{21}H_{13}F_7N_4O_2$: Calc.: %C, 51.9; %H, 2.69; %N, 11.5 Found: %C, 51.5; %H, 2.78; %N, 11.6; and 4,5-dihydro-3-(4-fluorophenyl)-4-(2-trifluoromethyl-5-thiazolyl)-N-(4-trifluoromethoxyphenyl)-1H-pyrazole-1-carboxamide (Compound I-Q), a white solid melting at 159.5°–161° C. (28 percent yield);

Elemental Analysis for $C_{21}H_{13}F_7N_4O_2S$: Calc.: %C, 48.9; %H, 2.53; %N, 10.8; %S, 6.18 Found: %C, 48.6; %H, 2.45; %N, 10.9; %S, 5.98.

EXAMPLE 10

Preparation of 2-(5-Chloro-2-thiazolyl)-1-(4-fluorophenyl)propanone

4-Fluoropropiophenone (3.04 g, 20 mmol) was added over a 10-min period to a slurry of potassium hydride (5.5 g of 35 percent in oil washed 3 times with hexanes (48 mmol)) in 50 mL of dry tetrahydrofuran at ambient temperature with stirring under nitrogen. The mixture was allowed to react for 15 min and was then cooled to 0° to −10° C. 2,5-Dichlorothiazole (3.39 g, 22 mmol) was then added over a 15-min period with stirring and the reaction was allowed to proceed under those conditions for 8 hr. The resulting mixture was extracted with water, dried over magnesium sulfate, filtered, and concentrated by evaporation under reduced pressure. The residue was kugelrohr distilled at 100°–110° C. and 0.02 torr (2.7 Pa) pressure to obtain 4.71 g (87 percent of theory) of the title compound as a yellow oil which tended to darken on standing.

Elemental Analysis for $C_{12}H_9ClFNOS$: Calc.: %C, 53.4; %H, 3.36; %N, 5.19; %S, 11.9 Found: %C, 54.6; %H, 3.91; %N, 5.24; %S, 11.2.

EXAMPLE 11

Preparation of 2-(5-Chloro-2-thiazolyl)-1-(4-fluorophenyl)-2-(phenylselenenyl)propanone A solution of 1.35 g (5.0 mmol) of 2-(5-chloro-2-thiazolyl)-1-(4-fluorophenyl)propanone in 2 mL of dry tetrahydrofuran was added over a 10-min period to a slurry of sodium hydride (240 mg of 60 percent in oil washed 3 times with hexane (6.0 mmol)) in 30 mL of dry tetrahydrofuran with stirring under nitrogen. The resulting mixture was cooled to −70° C. and 1.15 g (6.0 mmol) of phenylselenenyl chloride (recrystallized from hexanes shortly before use) dissolved in 5 mL of tetrahydrofuran was added by means of a dropping funnel with stirring under nitrogen over a 10-min period. The mixture was allowed to warm to ambient temperature and was then extracted with water, dried over magnesium sulfate, filtered, and concentrated by evaporation under reduced pressure. The residual oil was purified by medium pressure liquid chromatography eluting with a 9:1 mixture of hexanes and ethyl acetate to obtain 1.68 g (79 percent of theory) of the title compound as a yellow oil.

EXAMPLE 12

Preparation of 4-(5-Chloro-2-thiazolyl)-4,5-dihydro-3-(4-fluorophenyl)-N-(4-trifluoromethylphenyl)-1H-pyrazole-1-carboxamide (Compound I-O)

A slurry of dried meta-chloroperbenzoic acid (861 mg of 50–60 percent purity (2.5 mmol)) in 10 mL of dichloromethane was added to a solution of 1.06 g (2.5 mmol) of 2-(5-chloro-2-thiazolyl)-1-(4-fluorophenyl)-2-(phenylselenenyl)propanone in 25 mL of dichloromethane at −50° C. under nitrogen with stirring. The mixture was allowed to warm to −25° C. for a few minutes and was then cooled to −60° C. and pressure filtered. The filtrate was allowed to warm to −25° C. for a few minutes. It was then cooled to −60° C. and 160 uL (5.0 mmol) of anhydrous hydrazine was added with vigorous stirring. The mixture was allowed to warm to −25° C. for about 30 min and then 1 mL of trifluoroacetic acid was added and the reaction was allowed to proceed for another 20 min. The resulting solution was extracted with 50 mL of water and 50 mL of saturated aqueous sodium bicarbonate, dried over sodium sulfate and filtered to obtain 4-(5-chloro-2-thiazolyl)-4,5-dihydro-3-(4-fluorophenyl)-1H-pyrazole. The solution was then treated with 372 mg (2.0 mmol) of 4-trifluoromethylphenyl isocyanate at reflux with stirring for 15 min. The resulting mixture was allowed to cool, extracted with water, dried over sodium sulfate, filtered, and concentrated by evaporation under reduced pressure. The residual oil was purified by medium pressure liquid chromatography eluting with a 9:1 mixture of hexanes and ether to obtain a solid which was recrystallized from a mixture of hexanes and acetone to obtain 150 mg (13 percent of theory) of the title compound as a white solid melting at 187.5°–189° C.

Elemental Analysis for $C_{20}H_{13}ClF_4N_4OS$: Calc.: %C, 51.2; %H, 2.79; %N, 12.0; %S, 6.84 Found: %C, 51.3; %H, 2.91; %N, 12.0; %S, 6.54.

The compound 4-(5-chloro-2-thiazolyl)-4,5-dihydro-3-(4-fluorophenyl)-N-(4-trifluoromethoxyphenyl)-1H-pyrazole-1-carboxamide (Compound I-N) was prepared similarly and was a fluffy white solid melting at 172°–173.5° C.

Elemental Analysis for $C_{20}H_{13}ClF_4N_4O_2S$: Calc.: % C, 49.5; % H, 2.70; % N, 11.6; % S, 6.61 Found: % C, 48.4; % H, 2.58; % N, 11.1; % S, 5.78.

EXAMPLE 13

Effect on Tobacco Budworm and Beet Armyworm by Leaf Ingestion and/or Contact

Stock solutions of the compounds to be tested having a known concentration were prepared by dissolving weighed amounts in high-purity acetone and these solutions were diluted with distilled water (containing 0.05 percent by weight Triton X-155 TM surfactant) to obtain the spray solutions of known concentration employed. Greenhouse-grown cotton leaves of uniform age were cut into 2.5 cm diameter discs and one disc was placed in the bottom of each of a number of 30 mL plastic cups. The cups were then sprayed by means of a track sprayer applying 0.055 mL of spray solution per cup. The leaf discs were allowed to dry and then a single second-instar *H. virescens* (tobacco budworm) or *S. exigua* (beet armyworm) larva was added to each cup and each cup was capped with a plastic lid. Ten cups were prepared for each insect species and each application rate and five or six application rates were usually run. Treated cups were stored for 6 days at 25° C. and were then graded for mortality. Untreated controls and positive controls (cypermethrin) were run simultaneously. The amount of test chemical required to kill half of the larvae ($LD_{50}$) was calculated. Typical results are given in the following table.

| INSECTICIDAL ACTIVITY OF LEPIDOPTERA | | | |
|---|---|---|---|
| | Contact and Ingestion Test | Contact Test | Contact and Ingestion Test | Contact Test |
| Compound | $LC_{50}$, ppm | $LC_{50}$, ppm | $LC_{50}$, ppm | $LC_{50}$, ppm |
| I-A | 8.4 | <6.3 | 8.1 | 14.9 |
| I-B | 4.1 | 2.9 | 5.1 | 23 |
| I-C | 6.6 | 4.6 | 5.3 | 41 |
| I-D | >10 | — | >10 | — |
| I-E | 28 | — | >40 | — |
| I-F | 9.1 | — | 35 | — |
| I-G | >40 | — | >40 | — |
| I-H | >40 | — | >40 | — |
| I-I | 5.0 | 5.4 | 7.9 | 35 |
| I-J | 2.2 | — | 10 | — |
| I-K | 3.0 | 2.4 | 2.7 | 23 |
| I-L | 3.1 | 3.4 | 2.8 | 35 |
| I-M | 5.5 | 4.5 | 2.5 | >50 |
| I-N | 6.0 | <3.1 | 2.9 | 17 |
| I-O | 3.5 | 3.0 | 2.2 | 8.7 |

21

-continued

| | INSECTICIDAL ACTIVITY OF LEPIDOPTERA | | | |
|---|---|---|---|---|
| Compound | Contact and Ingestion Test LC$_{50}$, ppm | Contact Test LC$_{50}$, ppm | Contact and Ingestion Test LC$_{50}$, ppm | Contact Test LC$_{50}$, ppm |
| I-P | 1.1 | 9.9 | 5.3 | 22 |
| I-Q | 1.7 | 13 | 2.5 | >50 |

EXAMPLE 14

Effect on Tobacco Budworm and Beet Armyworm by Contact

Stock solutions of the compounds to be tested having a known concentration were prepared by dissolving weighed amounts in high-purity acetone and these solutions were diluted with distilled water (containing 0.5 percent by weight Triton X-155 TM surfactant) to obtain the spray solutions of known concentration employed. Plastic 5.5 cm diameter Petri dish bottoms and lids were sprayed on the inside surfaces by means of a track sprayer applying 0.104 mL of spray solution per dish. The Petri dishes were allowed to dry and then a single second-instar *H. virescens* (tobacco budworm) or *S. exigua* (beet armyworm) larva was placed on each Petri dish bottom and a lid was placed on each bottom. Ten Petri dishes were prepared for each application rate and at least four application rates were usually run. Treated Petri dishes were stored for 24 hours at 25° C. and then the larvae was transferred to a 30 mL plastic cup containing an untreated cotton leaf disc. After 5 more days of storage at 25° C. the dishes were graded for mortality. Untreated controls and positive controls (cypermethrin) were run simultaneously. The amount of test chemical required to kill half of the larvae (LD$_{50}$) was calculated. Typical results are given in the preceding table.

EXAMPLE 15

Effect on Cockroaches

Two hundred ppm stock solutions of the compounds to be tested were prepared by dissolving 2.4 milligrams (mg) of each test compound in 12 mL of acetone and four lower concentration solutions were prepared by serial dilution using 3 mL of solution. A 0.5 mL portion of each test solution was pipetted onto 0.2 g of yellow corn meal placed in a small test tube cap (Fisher 02-706-33) and the mixture was placed in a fume hood overnight to allow the solvent to evaporate. This resulted in diets containing 500, 125, 31.2, 7.8, and 2.0 ppm of the test compounds to be used to determine activity by ingestion. Each cap was then placed in a 9 cm diameter Petri plate along with a 2 dram vial containing a cotton wick and water. A 0.5 mL portion of each test solution was also pipetted into a 20 mL borosilicate glass scintillation vial. The vials were placed on a roller mixer and the acetone was allowed to evaporate while the vials rolled. This resulted in vial walls containing 2.5, 0.63, 0.16, 0.04, and 0.01 micrograms/cm$^2$ to be used to determine activity by contact. Five late third or early fourth instar *Blattella germanica* nymphs weighing 0.01–0.04 g were placed in each vial and each Petri plate and covers were applied loosely to allow entry of air.

22

Each Petri plate and vial was held at 27° C., the Petri plates for 21 days and the vials for 7 days. The percent of mortality was read periodically and at the end of the test. Some of the compounds that were active in this test are listed in the following table.

| Compound | Dose giving ≧95% control after 7 days, ppm (contact test) | Dose giving ≧95% control after 21 days, ppm (ingestion test) |
|---|---|---|
| B | >200 | 200 |
| O | >200 | >200 |
| P | 12.5 | 12.5 |
| Q | 200 | 50 |

What is claimed is:

1. A 1,2-diarylethanone compound of the formula

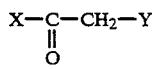

wherein

Y represents a 5-membered aromatic heterocyclic ring moiety containing one ring oxygen or sulfur atom and one ring nitrogen atom, which moiety is attached through a carbon atom and is optionally substituted with one substituent selected from F, Cl, Br, CN, COQ, R, OR', SR', SOR', SO$_2$R', NO$_2$, and OAr and optionally additionally substituted with a F substituent;

X represents phenyl optionally substituted in the 4-position with F, Cl, Br, CN, COQ, R, OR', SR', SOR', SO$_2$R', NO$_2$, or OAr and/or in the 3-position with F, Cl, Br, CN, R, or OR';

R represents C$_1$-C$_3$ alkyl, C$_2$-C$_3$ alkenyl, or C$_2$-C$_3$ alkynyl optionally singly to completely substituted with fluorine or chlorine;

R' represents C$_1$-C$_3$ alkyl optionally singly to completely substituted with fluorine or chlorine;

Ar represents phenyl optionally substituted with 1 or 2 compatible substituents selected from F, Cl, Br, CN, COQ, R, OR', SR', SOR', SO$_2$R', and NO$_2$;

Q represents OR$^2$, SR$^2$, NH$^2$, NHR$^2$, OR NR$^2$$_2$; and

R2 represents C$_1$-C$_4$ alkyl, C$_3$-C$_4$ alkenyl, or C$_3$-C$_4$ alkynyl.

2. A compound according to claim 1 wherein X represents phenyl substituted in the 4-position with F, Cl, Br, CF$_3$, OCF$_3$, OCF$_2$H, OCF$_2$CF$_2$H, SO$_2$CF$_3$, or SCF$_3$.

3. A compound according to claim 1 wherein Y represents a thiazolyl or oxazolyl moiety attached at one position adjacent to the oxygen or sulfur atom and possessing one of the designated substituents in the other position adjacent to the oxygen or sulfur atom.

4. A compound according to claim 3 wherein the substituent is selected from F, Cl, Br, CN, OCF$_3$, OCF$_2$H, and CF$_3$.

5. A compound according to claim 1 selected from 1-(4-fluorophenyl)-2-(2-trifluoromethyl-5-thiazolyl)ethanone, 2-(5-chloro-2-thiazolyl)-1-(4-fluorophenyl)ethanone, 1-(4-fluorophenyl)-2-(2-trifluoromethyl-5-oxazolyl)ethanone, and 1-(4-fluorophenyl)-2-(3-trifluoromethyl-5-isothiazolyl)ethanone.

* * * * *